United States Patent
Azapagic et al.

(10) Patent No.: US 10,366,788 B2
(45) Date of Patent: Jul. 30, 2019

(54) ADMINISTRATION SET DETECTION AND AUTHENTICATION USING CAM PROFILES

(71) Applicant: Curlin Medical Inc., East Aurora, NY (US)

(72) Inventors: Azur Azapagic, Cottonwood Heights, UT (US); Mohan Jonathan Barkley, Salt Lake City, UT (US)

(73) Assignee: Curlin Medical Inc., East Aurora, NY (US)

( * ) Notice: Subject to any disclaimer, the term of this patent is extended or adjusted under 35 U.S.C. 154(b) by 206 days.

(21) Appl. No.: 15/243,438

(22) Filed: Aug. 22, 2016

(65) Prior Publication Data
US 2018/0050153 A1    Feb. 22, 2018

(51) Int. Cl.
*A61M 5/142* (2006.01)
*A61M 5/168* (2006.01)
*G16H 40/63* (2018.01)

(52) U.S. Cl.
CPC ........ *G16H 40/63* (2018.01); *A61M 5/14228* (2013.01); *A61M 5/16881* (2013.01); *A61M 2205/14* (2013.01); *A61M 2205/332* (2013.01); *A61M 2205/3306* (2013.01); *A61M 2205/3317* (2013.01); *A61M 2205/3375* (2013.01); *A61M 2205/502* (2013.01); *A61M 2205/52* (2013.01); *A61M 2205/60* (2013.01)

(58) Field of Classification Search
CPC .................. A61M 5/14228; A61M 5/16881
See application file for complete search history.

(56) References Cited

U.S. PATENT DOCUMENTS

| | | | |
|---|---|---|---|
| 5,431,627 A | 7/1995 | Pastrone et al. | |
| 5,531,698 A | 2/1996 | Olsen | |
| 5,531,697 A | 7/1996 | Olsen et al. | |
| 5,683,367 A | 11/1997 | Jordan et al. | |
| 5,840,058 A | 11/1998 | Ammann et al. | |
| 6,077,055 A | 6/2000 | Vilks | |
| 6,123,686 A | 9/2000 | Olsen et al. | |
| 6,164,921 A * | 12/2000 | Moubayed | A61M 5/14228 417/44.1 |
| 6,371,732 B1 | 4/2002 | Moubayed et al. | |
| 8,679,075 B2 | 3/2014 | Lurvey et al. | |
| 2007/0135766 A1 | 6/2007 | Fournie et al. | |
| 2010/0204651 A1 | 8/2010 | Stringham | |
| 2012/0130676 A1 | 5/2012 | Zhou | |
| 2013/0336814 A1 * | 12/2013 | Kamen | A61M 5/16859 417/302 |

\* cited by examiner

*Primary Examiner* — Rebecca E Eisenberg
*Assistant Examiner* — Tasnim Mehjabin Ahmed
(74) *Attorney, Agent, or Firm* — Hodgson Russ LLP (57) ABSTRACT

An administration set for an infusion pump includes a free-flow prevention device having a movable plunger that includes a cam surface defining an uneven profile along a direction of movement of the plunger, wherein the shape of the cam surface profile indicates the administration set is authorized for use with the infusion pump and may further indicate the specific type of administration set. A sensor in the infusion pump senses movement of the plunger as a platen of the infusion pump is latched and generates a profile signal in the time domain representative of the cam surface profile. A processor evaluates the profile signal and controls operation of the pump to protect a patient from improper loading of an administration set, use of an unauthorized administration set, and/or use of an invalid type of administration set for a chosen infusion protocol.

6 Claims, 8 Drawing Sheets

ADMINISTRATION SET DETECTION AND AUTHENTICATION USING CAM PROFILES

FIELD OF THE INVENTION

The present invention relates generally to infusion pumps for controlled delivery of liquid food and medications to patients. More specifically, the present invention relates to a sensor system for detecting whether or not an administration tubing set is operatively connected to an infusion pump.

BACKGROUND OF THE INVENTION

Programmable infusion pumps are used to carry out controlled delivery of liquid food for enteral feeding and medications for various purposes, for example pain management. In a common arrangement, an infusion pump receives a disposable administration set comprising flexible tubing having a tubing segment designed to be engaged by a pumping mechanism of the infusion pump. The administration set may further comprise a pair of mounting components fixedly attached to the flexible tubing at predetermined locations at or near opposite ends of the tubing segment, whereby the mounting components are receivable by respective mating features on the infusion pump to secure the tubing segment in proper position for operative engagement by the pumping mechanism. One of the mounting components may provide additional functionality beyond helping to properly locate the tubing segment. For example, one of the mounting components may be configured as a free-flow prevention device operable to selectively stop and permit flow of the infusion liquid through the tubing. Upon loading the administration set in the pump, the free-flow prevention device is actuated from its normal flow-stopping closed position to its open position allowing flow. An example of the arrangement described above is disclosed in U.S. Pat. No. 6,164,921 to Moubayed et al.

It is known to provide different types of administration sets all of which are intended for use with a particular infusion pump model or models. The various types of administration sets may be distinguishable from one another according to design specifications that are chosen based on the specific intended use of the administration set. For example, the tubing segment of the administration set may be dimensioned with a specific inner diameter and wall thickness for carrying certain liquid formulations of known viscosity, and may be formed of a material having a specific durometer. The material durometer, inner diameter, and wall thickness of the tubing segment are held within close manufacturing tolerances to ensure that the administration set provides intended flow characteristics when the tubing segment is acted upon by the pumping mechanism of the infusion pump.

Various types of administration sets may also be distinguishable from one another based on coupling hardware and other structural features provided as part of the administration set. For example, an end of the administration set may be provided with a bag for storing liquid, a vented vial spike, or a non-vented spike. As another example, the administration set may include a filter of a predetermined pore size, or it may not include a filter. Other structural features that may or may not be included in a particular administration set are an anti-siphon valve and a Y-connector having a check valve.

For safety reasons, it is desirable to ensure that the type of administration set chosen for use with a particular infusion pump to deliver an intended infusion protocol is the proper administration set. As an initial matter, it is desirable to confirm that an administration set is installed in the infusion pump. The installed administration set should be authentic from the standpoint that it is approved by the infusion pump manufacturer for use with the infusion pump. The installed administration set should also be of a type that is configured for delivering a selected infusion protocol which the infusion pump is programmed to execute.

What is needed is an administration set detection and authentication scheme that is easily implemented without adding hardware to the administration set or the infusion pump, that determines whether or not an administration set is installed and is authentic, and that distinguishes among different types of authentic administration sets to identify the type of administration set that is installed.

SUMMARY OF THE INVENTION

In accordance with the present invention, a free-flow prevention device for controlling flow of an infusion liquid through tubing of an administration set comprises a movable plunger that includes a cam surface defining an uneven profile along a direction of movement of the plunger, wherein the shape of the cam surface profile indicates the administration set is authorized for use with the infusion pump and may further indicate the type of administration set.

A sensor in the infusion pump is arranged to sense movement of the plunger as a platen of the infusion pump is latched thereby moving the plunger from a closed position to an open position. As the plunger is moved, the cam surface of the plunger displaces a follower in contact with the cam surface, and the sensor detects displacement of the follower to generate a profile signal in the time domain representative of the cam surface profile.

A processor compares the profile signal to stored reference values corresponding to various predetermined authorized profiles, and determines whether or not the administration set is loaded in the infusion pump and whether or not the administration set is authorized for use with the infusion pump. If the administration set is not properly loaded or is not authorized, the processor sends a command disabling operation of the infusion pump. The processor may also determine the specific type of the administration set from among a plurality of administration set types, and send a command disabling operation of the pump if the determined type of the administration set is incompatible with a desired infusion protocol entered into the infusion pump by a user.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1A:
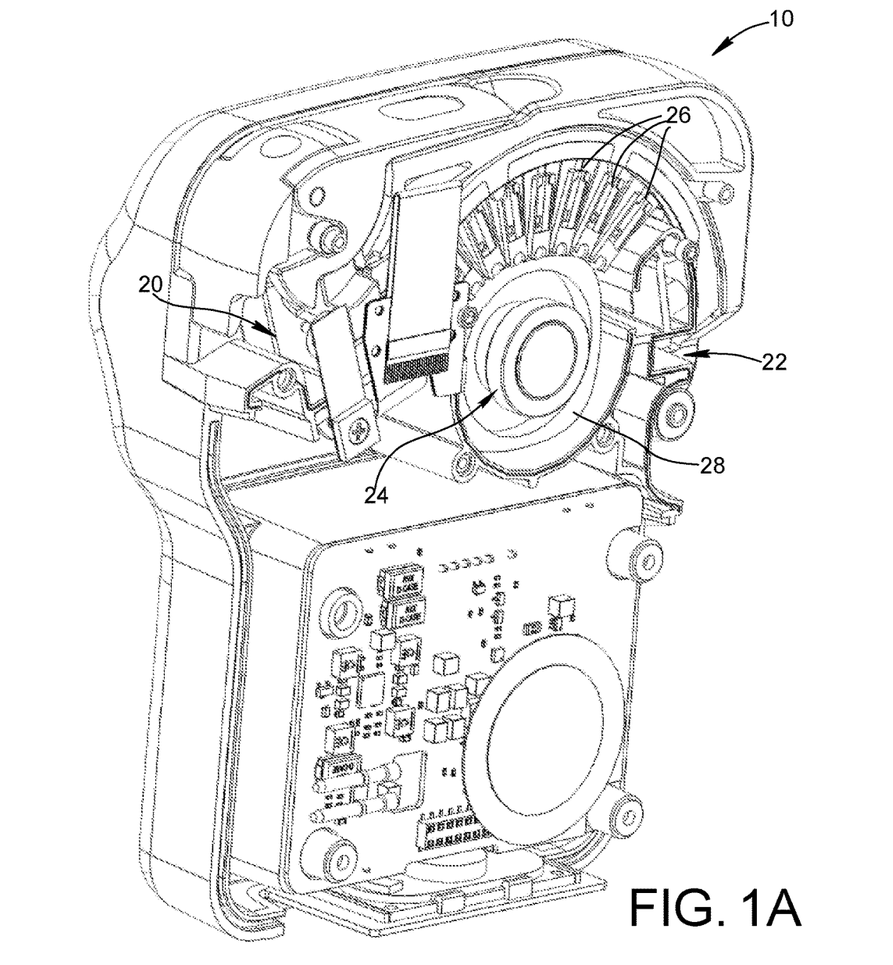
FIG. 1A is perspective view of an infusion pump formed in accordance with an embodiment of the present invention, wherein a front cover of the infusion pump is removed to reveal internal structure.
Figure 1B:
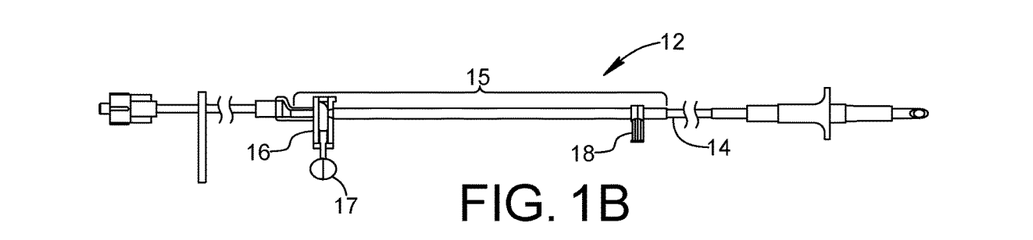
FIG. 1B is a view showing an administration set formed in accordance with an embodiment of the present invention for use in the infusion pump shown in FIG. 1A.

FIG. 1A shows an infusion pump 10 and FIG. 1B shows a disposable administration set 12 designed to be removably received by infusion pump 10. Administration set 12 comprises tubing 14 for conveying an infusion liquid, and a free-flow prevention device 16 operable to selectively stop and permit flow of the infusion liquid through the tubing 14.

Administration set 12 may also comprise a locator pin 18. Free-flow prevention device 16 and locator pin 18 may be fixedly attached to tubing 14 at separate locations along the tubing. For example, free-flow prevention device 16 and locator pin 18 may be bonded to tubing 14 by a bonding agent. As may be seen in FIG. 1A, infusion pump 10 has a first recess 20 sized to removably receive free-flow prevention device 16, and a second recess 22 sized to removably receive locator pin 18. Administration set 12 is loaded into infusion pump 10 by inserting free-flow prevention device 16 into first recess 20 and locator pin 18 into second recess 22 such that a segment 15 of tubing 14 wraps around a pumping mechanism 24 of pump 10. Free-flow prevention device 16 may include a breakaway detent tab 17 for maintaining free-flow prevention device 16 in an open condition prior to loading of administration set 12 in pump 10. In the illustrated embodiment, pumping mechanism 24 is a peristaltic pumping mechanism having a plurality of extendable and retractable pumping fingers 26 that are moved by rotation of a motor-driven eccentric cam 28 to engage tubing segment 15 in sequential peristaltic fashion such that liquid is pumped through tubing 14.

Figure 2:
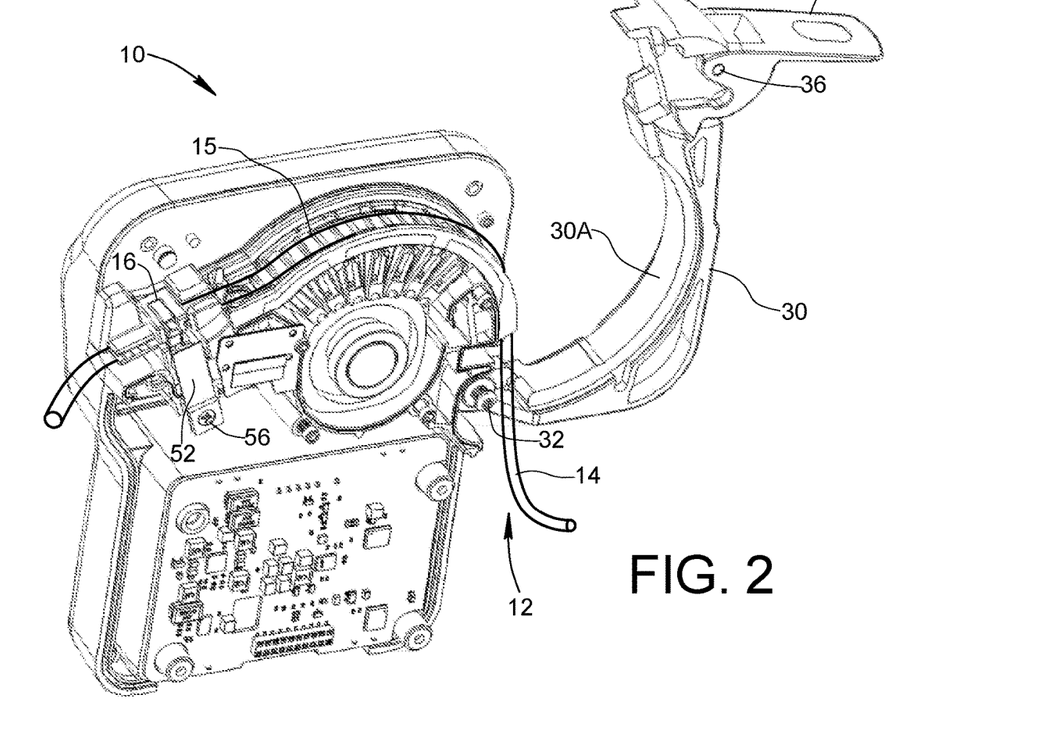
FIG. 2 is another perspective view of the infusion pump and administration set shown in FIG. 1, however a platen of the infusion pump is shown in an open position for loading or unloading the administration set.
Figure 3:
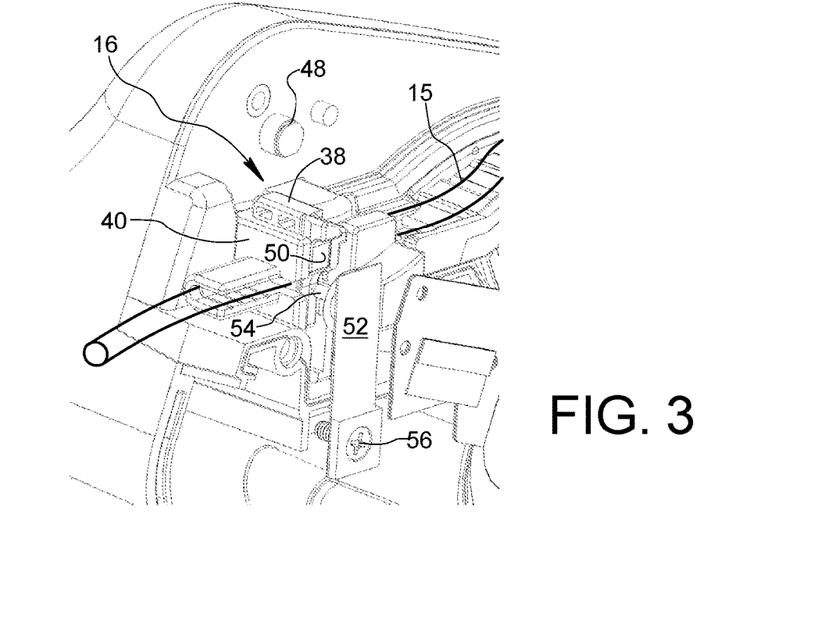
FIG. 3 is a detailed perspective view showing a free-flow prevention device of the administration set received by the infusion pump.

As may be seen in FIG. 2, infusion pump 10 includes a platen 30 pivotally mounted at a pivot pin 32. Platen 30 has a platen surface 30A that comes into contact with tubing segment 15 opposite pumping fingers 26 when platen 30 is pivoted down toward pumping mechanism 24. A locking latch 34 is pivotally mounted at a free end of platen 30 by a pivot pin 36. As will be described in detail below, locking latch 34 is operable to secure platen 30 in a closed position on infusion pump 10 with platen surface 30A contacting tubing segment 15 in preparation for starting a pumping protocol. Locking latch 34 further serves as an actuating member for moving a plunger 38 of free-flow prevention device 16, visible in FIG. 3, relative to a carrier 40 of free-flow prevention device 16.

Figure 4A:
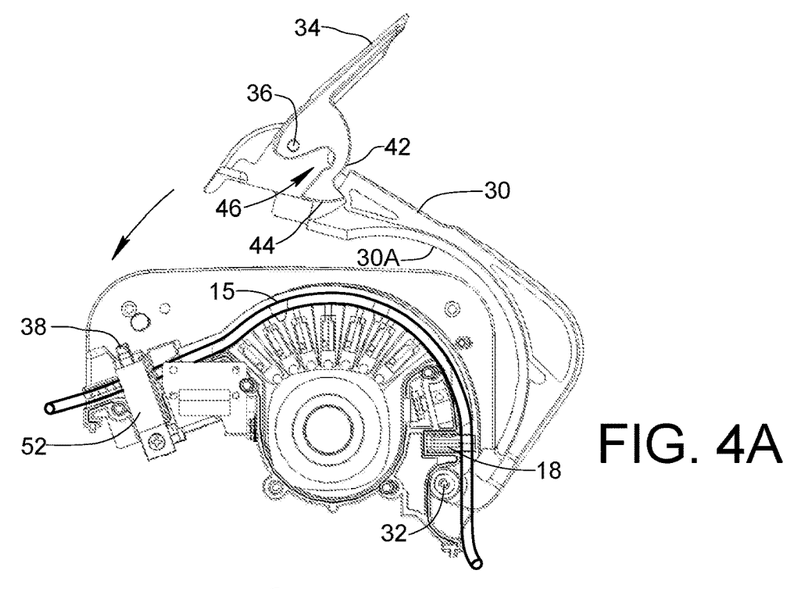
FIG. 4A is a front elevational view showing the administration set and an upper pumping mechanism of the infusion pump, wherein the platen is in the open position and a locking latch associated with the platen is in an unlocked position.
Figure 4B:
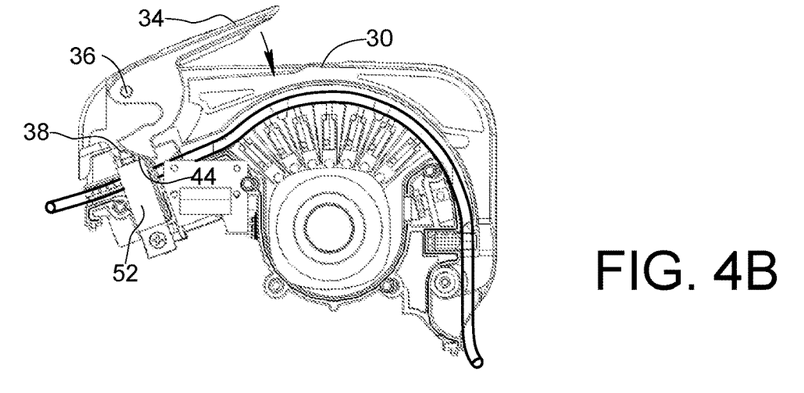
FIG. 4B is a view similar to that of FIG. 4A, wherein the platen is pivoted toward a closed position and the locking latch is partially pivoted from the unlocked position toward the locked position.
Figure 4C:
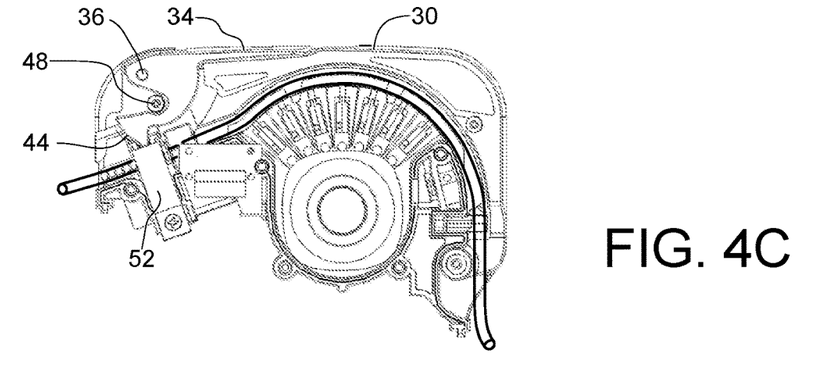
FIG. 4C is a view similar to that of FIG. 4B, wherein the platen is pivoted into the closed position and the locking latch is fully pivoted into the locked position.
Figure 5:
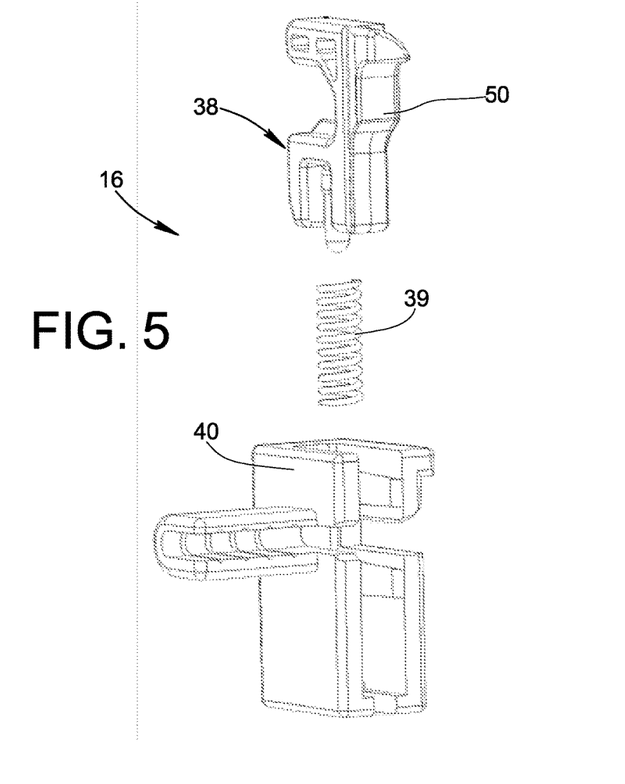
FIG. 5 is an exploded perspective view of the free-flow prevention device of the administration set.

FIGS. 4A-4C illustrate closure of platen 30 and operation of locking latch 34 after administration set 12 is positioned in pump 10. Platen 30 is pivoted counterclockwise until a drive arm 42 of locking latch 34 contacts a top portion of plunger 38, and then locking latch 34 is pivoted clockwise relative to platen 30 such that a curved surface 44 at the end of drive arm 42 forces plunger 38 to move downward relative to carrier 40. As locking latch 34 is pivoted, a jaw opening 46 on each side of the locking latch securely mates with a corresponding lateral protrusion 48 of the infusion pump body to lock platen 30 in its closed operating position.

Figure 6A:
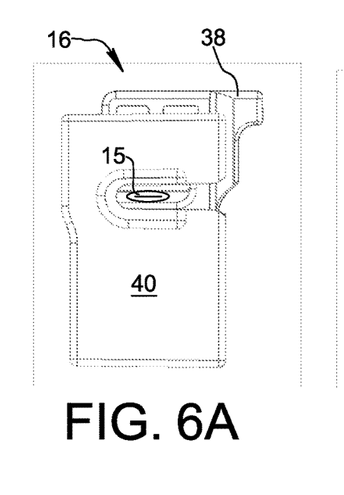
FIG. 6A is an elevational view of the free-flow prevention device looking axially along tubing of the administration set, wherein a plunger of the free-flow prevention device is in a closed position relative to a carrier of the free-flow prevention device.
Figure 6B:
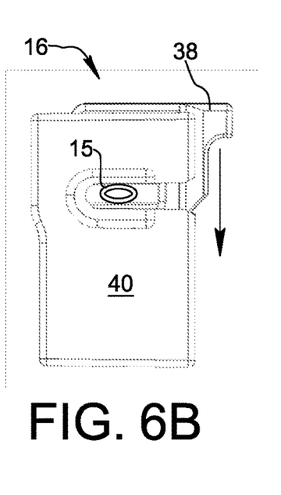
FIG. 6B is a view similar to that of FIG. 6A, wherein the plunger is moved relative to the carrier away from the closed position and toward an open position.
Figure 6C:
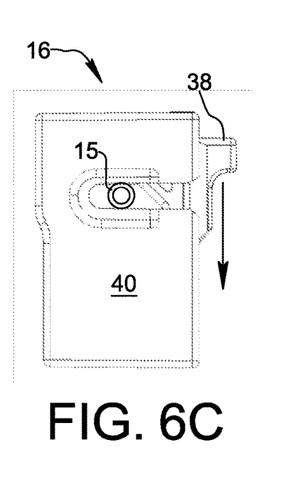
FIG. 6C is a view similar to that of FIG. 6B, wherein the plunger is in the open position relative to the carrier.

In accordance with the present invention, the movement of plunger 38 is sensed in the time domain and provides information for detecting and authenticating administration set 12. In an embodiment of the invention, plunger 38 includes a cam surface 50 defining an uneven profile along a direction of movement of the plunger, wherein the uneven profile of cam surface 50 indicates that administration set 12 is authorized for use with infusion pump 10, and further indicates the type of administration set 10. The basic operation of free-flow prevention device 16 may be understood from FIGS. 5 and 6A-6C. Plunger 38 is mounted in carrier 40 for sliding reciprocal motion relative to the carrier between a closed position (FIG. 6A) in which respective tube openings in the plunger and carrier are misaligned to pinch tubing segment 15 closed to prevent flow through tubing 14, and an open position (FIG. 6C) in which respective tube openings in the plunger and carrier are substantially aligned so that tubing segment 15 is not pinched closed and flow is permitted through tubing 14. A spring 39 acts between carrier 40 and plunger 38 to bias plunger 38 toward the closed position shown in FIG. 6A. As may be understood, plunger 38 must be moved against the biasing force of spring 39 to move plunger from the closed position to the open position. As explained above with reference to FIGS. 4A-4C, such force is provided by pivoting locking latch 34 relative to platen 30 so that curved surface 44 at the end of drive arm 42 moves plunger 38 downward relative to carrier 40. Plunger 38 is held in the open position when platen 30 is secured by locking latch 34. When locking latch 34 is pivoted counterclockwise in FIG. 4C to allow platen 30 to be opened, plunger 38 is allowed to move under force of spring 39 to the closed position to prevent free flow. In addition to the basic operation of free-flow prevention device 16, the movement of plunger 38 provides a detectable signature that depends on the profile of the plunger's cam surface 50.

Infusion pump 10 comprises a sensor 52 arranged to sense the movement of plunger 38 relative to carrier 40. Sensor 52 generates a profile signal in the time domain representative of the profile of cam surface 50. In an embodiment of the invention illustrated by FIGS. 7A-7C, sensor 52 may be a strain gauge and infusion pump 10 may comprise a follower 54 biased for continuous engagement with cam surface 50 of plunger 38 when free-flow prevention device 16 is loaded in the infusion pump, wherein cam surface 50 slidably engages follower 54 to displace the follower laterally as plunger 38 is moved from the closed position to the open position. Sensor 52 has one end portion attached by a fastener 56 to a fixed structural member of pump 10 (not shown), and another end portion engaged by follower 54, such that lateral displacement of follower 54 causes corresponding deflection of sensor 52. Sensor 52 and follower 54 may be arranged such that sensor 52 is slightly deflected even when plunger 38 is in the closed position represented by FIGS. 6A and 7A, such that a preload is applied by sensor 52 on follower 54 to maintain engagement of the follower with cam surface 50. The output signal generated by sensor 52 is proportional to the amount of deflection of the sensor. The behavior of the signal generated by sensor 52 in the time domain will depend on the profile shape of cam surface 50. Thus, by providing various predetermined profiles of cam surface 50 that share at least one feature among all profiles and differ from one another with respect to at least one other feature, the cam surface profiles may be used to confirm authenticity of an administration set 12 as being compatible with pump 10, and also to determine the specific type of the administration set from among a plurality of different administration set types all of which are compatible with pump 10.

Figure 7A:
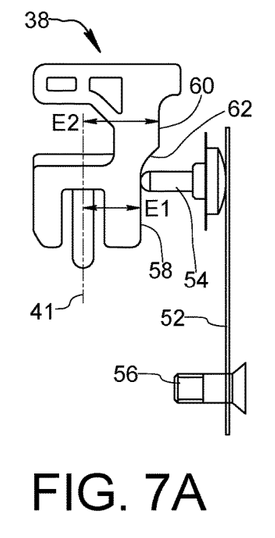
FIG. 7A is an elevational view showing the plunger operatively connected to a sensor of the pump by a follower, wherein the plunger is in the closed position and has a first cam surface profile.
Figure 7B:
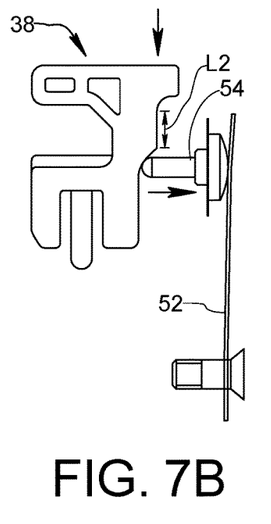
FIG. 7B is a view similar to that of FIG. 7A, wherein the plunger is moved away from the closed position and toward the open position, and the follower is displaced laterally to deform the sensor.
Figure 7C:
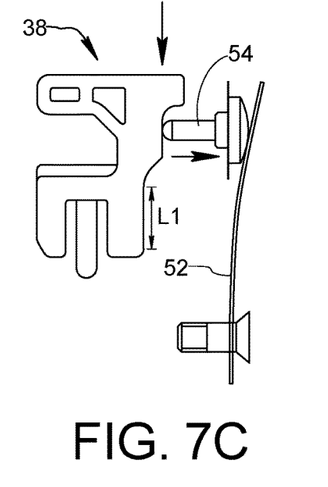
FIG. 7C is a view similar to that of FIG. 7B, wherein the plunger is moved into the closed position, and the follower is further displaced laterally to further deform the sensor.

In FIGS. 7A-7C, the profile of cam surface 50 includes a first plateau 58 and a second plateau 60 having different respective "elevations" E1 and E2. As used herein in reference to the profile of cam surface 50, the term "elevation" means a lateral distance from a central axis 41 along which plunger 38 moves. First plateau 58 and second plateau 60 may have different respective lengths L1 and L2 in the direction of movement of plunger 38. The profile of cam surface 50 may further include a topographical feature 62 between first plateau 58 and second plateau 60. In the embodiment shown in FIGS. 7A-7C, topographical feature 62 takes the form of a ramp between first plateau 58 and second plateau 60. Topographical feature 62 may take other forms, for example a bump or a recess.

Figure 8:
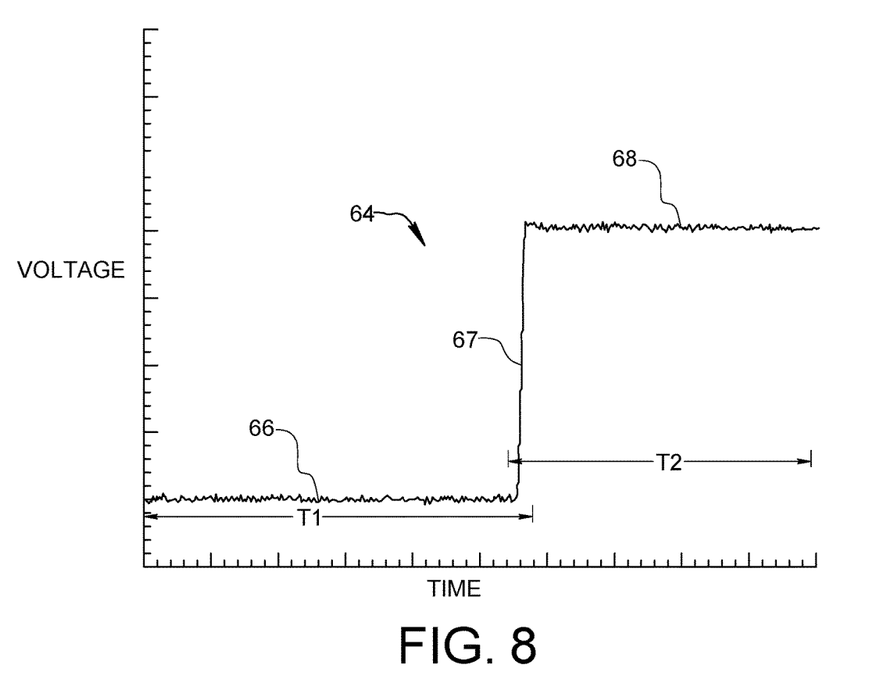
FIG. 8 is a plot showing amplitude versus time of a signal generated by the sensor in FIGS. 7A-7C.

FIG. 8 shows a voltage signal 64 versus time generated by sensor 52 in response to the downward motion of plunger 38 depicted by FIGS. 7A-7C. As may be seen, signal 64 has a first portion 66 of relatively low amplitude corresponding to first elevation E1, and a second portion 68 of relatively high amplitude corresponding to second elevation E2. Signal 64 also includes a transition portion 67 between first and second portions 66 and 68 characterized by changing amplitude.

Figure 9:
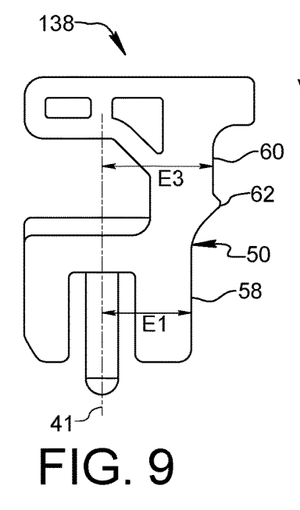
FIG. 9 is an elevational view of another plunger having a second cam surface profile differing from the first cam surface profile.
Figure 10:
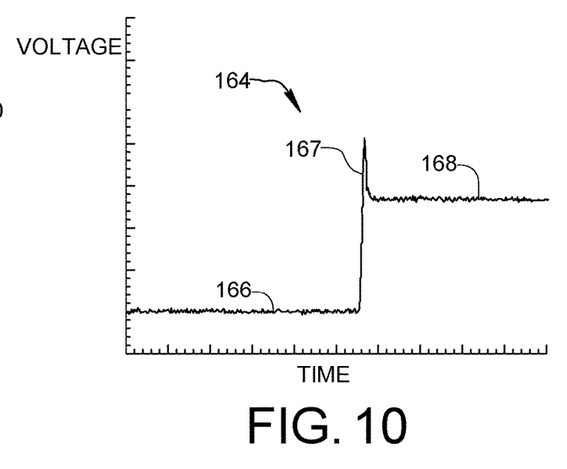
FIG. 10 is a plot showing amplitude versus time of a sensor signal responsive to movement of the plunger shown in FIG. 9 from the closed position to the open position.

FIG. 9 shows an alternative plunger 138 having another possible profile of cam surface 50. In plunger 138, the topographical feature 62 of cam surface 50 is a bump that rises in elevation and then drops down slightly as it transitions from first plateau 58 to second plateau 60. First plateau 58 has the same elevation E1 as that of the plunger 38 shown in FIGS. 7A-7C, however second plateau 60 has a different elevation E3 that is slightly less than the elevation E2 of plunger 38. FIG. 10 illustrates a voltage signal 164 versus time generated by sensor 52 in response to the downward motion of plunger 138. A first portion 166 of sensor signal 164 has the same amplitude as the first portion 66 of sensor signal 64 due to matching elevations of the first plateaus 58. A second portion 168 of sensor signal 164 has an amplitude greater than the amplitude of first portion 166, but less than the amplitude of second portion 68 of signal 64, owing to the fact that elevation E3 is less than elevation E2. A transition portion 167 of signal 164 is characterized by a significant increase in amplitude followed by a modest decrease in amplitude as determined by bump 62 in cam surface 50 of plunger 138.

Figure 11:
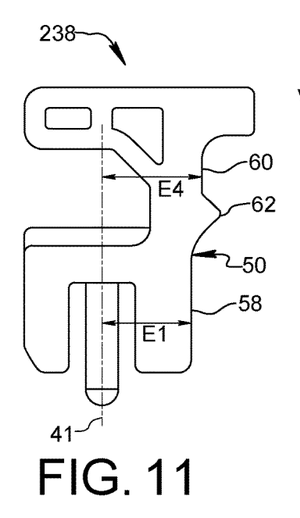
FIG. 11 is an elevational view of yet another plunger having a third cam surface profile differing from the first and second cam surface profiles.
Figure 12:
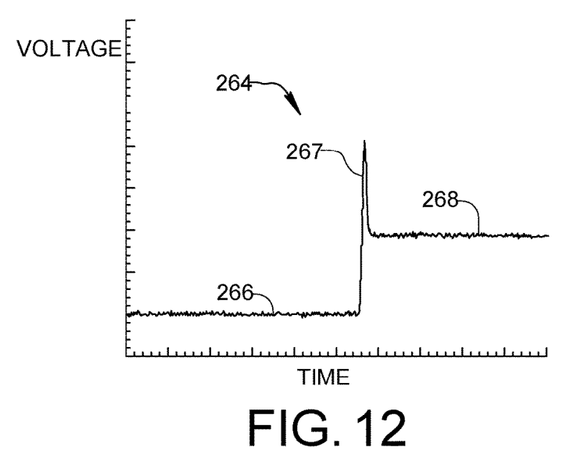
FIG. 12 is a plot showing amplitude versus time of a sensor signal responsive to movement of the plunger shown in FIG. 11 from the closed position to the open position.

FIG. 11 shows a further alternative plunger 238 having yet another possible profile of cam surface 50. In plunger 238, the topographical feature 62 of cam surface 50 is a bump that rises in elevation and then drops down significantly as it transitions from first plateau 58 to second plateau 60. First plateau 58 has the same elevation E1 as that of the plungers 38 and 138, however second plateau 60 has a different elevation E4 that is less than elevation E2 of plunger 38 and elevation E3 of plunger 138. FIG. 12 illustrates voltage signal 264 versus time generated by sensor 52 in response to the downward motion of plunger 238. A first portion 266 of sensor signal 264 has the same amplitude as the first portions 66 of sensor signals 64 and 164 due to matching elevations of the first plateaus 58. A second portion 268 of sensor signal 264 has an amplitude greater than the amplitude of first portion 266, but less than the amplitude of second portion 168 of signal 164 because elevation E4 is less than elevation E3. A transition portion 267 of signal 264 is characterized by a significant increase in amplitude followed by a decrease in amplitude as determined by bump 62 in cam surface 50 of plunger 238.

Thus, signals 64, 164, and 264 corresponding to plungers 38, 138, and 238 share similar signal portions, but are distinguishable from one another by other signal portions exhibiting different amplitudes and behaviors in the time domain. The similar signal portions may be used to determine the presence and authenticity of an administration set, whereas the different signal portions may be used to determine the specific type of administration set from a plurality of authentic administration sets authorized for use with infusion pump 10.

Figure 13:
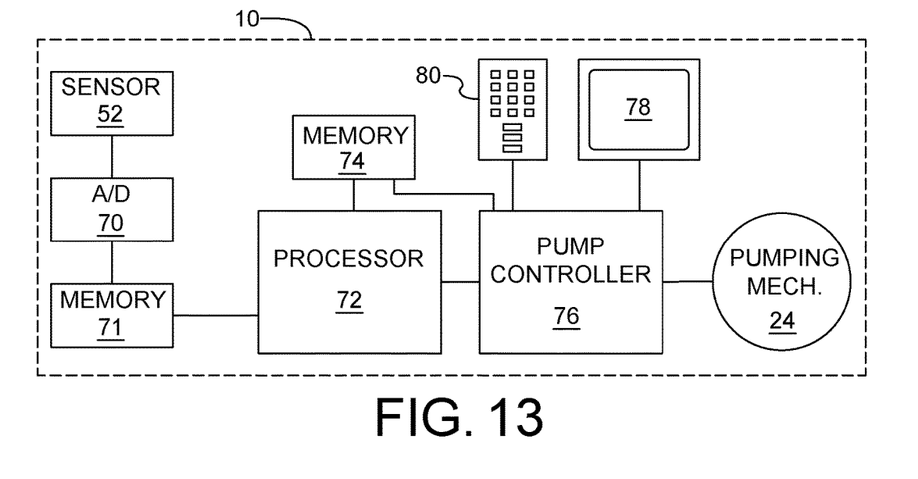
FIG. 13 is a schematic diagram showing signal processing electronics of the infusion pump shown in FIG. 1.

FIG. 13 is a schematic diagram showing signal processing electronics of infusion pump 10 used to evaluate profile signals generated by sensor 52. An analog signal from sensor 52 is converted to a digital signal by an analog-to-digital converter 70 and stored in a volatile memory 71. The digitized signal is then read by a processor 72 programmed to evaluate the signal. Processor 72 executes programming instructions stored in a non-volatile memory 74 associated with the processor 72. Memory 74 also stores predetermined reference values representing the various respective profile signals of each type of authorized administration set. The reference values may be stored, for example, in a lookup table that provides expected amplitude values at predetermined moments in time for each profile signal. Processor 72 executes programming instructions stored in memory 74 causing the processor to compare the digitized profile signal from sensor 52 to the stored reference values and determine whether or not the administration set is loaded in the infusion pump, and whether or not the administration set is authorized for use with the infusion pump, based on the comparison. Processor 72 may be in communication with a pump controller 76, or may itself act as the pump controller, whereby operation of pump 10 may be controlled based on an evaluation of the profile signal generated by sensor 52. Pump controller 76 is in communication with a user interface display screen 78 and a keypad 80 for inputting commands and parameters to the controller.

Figure 14:
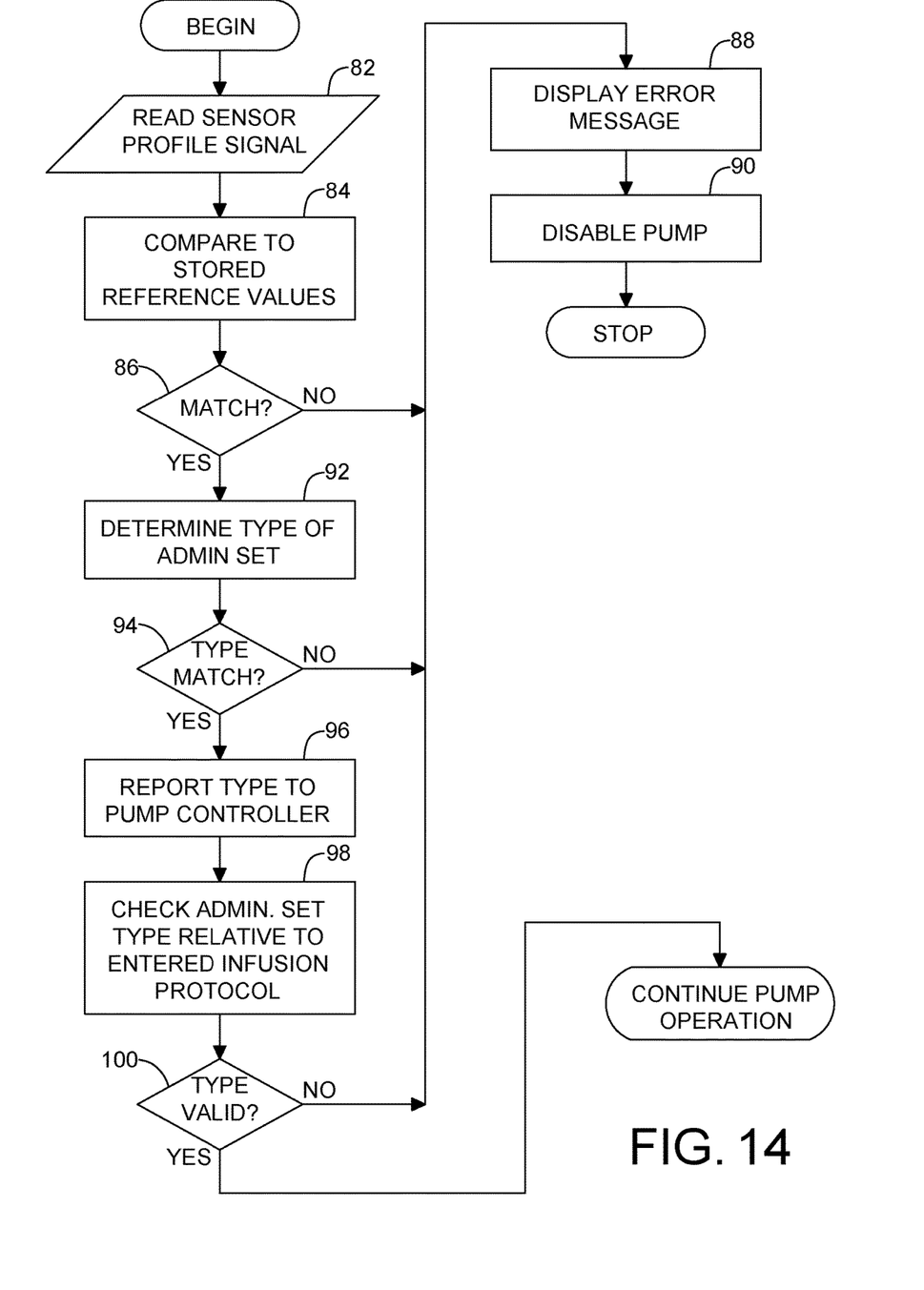
FIG. 14 is a flow diagram showing decision logic executed by the signal processing electronics in accordance with an embodiment of the present invention.

The flow diagram of FIG. 14 shows, in accordance with an embodiment of the invention, decision logic executed by processor 72 and/or controller 76 to evaluate a profile signal and control infusion pump 10 based on results of the evaluation. In block 82, the digitized profile signal stored in memory 71 is read by processor 52. A first comparison is performed in block 84 looking at a portion of the signal used to indicate presence and authenticity of an administration set. For example, a comparison of first portion 66, 166, 266 of the signal to corresponding stored reference values may be conducted. In decision block 86, flow branches based upon whether the comparison finds a match. If a match is not found, the administration set is determined to be improperly loaded and/or inauthentic, and flow is directed to blocks 88 and 90 to display an error message on display screen 78 and command controller 76 to disable operation of pump 10. Thus, the patient is protected from improper loading of an administration set even if the administration set is authorized, and the patient is also protected from use of an unauthorized administration set. If a match is found in block 86, then the administration set is deemed to be properly loaded and authentic, and flow continues to block 92.

In block 92, a further comparison is performed looking at a portion of the profile signal used to indicate the specific type of administration set. For example, a comparison of second portion 68, 168, 268 of the signal to corresponding stored reference values, and/or a comparison of transition portion 67, 167, 267 of the signal to corresponding stored reference values may be conducted. In decision block 94, flow branches based upon whether the further comparison finds a matching type. If a match is not found, the administration set is determined to be improperly loaded and/or inauthentic, and flow is directed to blocks 88 and 90. If a match is found in block 94, the corresponding administration set type is identified and reported as a parameter to pump controller 76 in accordance with block 96.

Pump controller 76 may be programmed to operate in a predetermined manner based on the identified type of administration set and an infusion protocol entered in pump 10 by a user. For example, in block 98, the identified type of administration set may be checked against a predetermined list of valid set types associated with the entered infusion protocol and stored in memory 74. In decision block 100, flow branches based upon whether or not the administration set type is valid for the selected infusion protocol. If not, flow is directed to block 88 to display an error message on display screen 78 indicating the administration set is the wrong type, and then to block 90 to disable operation of pump 10. If the detected administration set type is valid for use in delivering the selected infusion protocol, then pump operation continues in a normal manner. Thus, the present invention protects the patient if the wrong type of administration set is loaded for a desired infusion protocol, even if the administration set is authentic.

Comparisons between the sensed profile signal and the stored predetermined reference values representing various recognized profile signals may be made in different ways. Amplitude values of the sensed profile signal may be sampled at predetermined times and compared to corresponding stored values. Comparisons may also involve determining a time duration that the sensed profile signal remains at a given amplitude level before the amplitude changes, and comparing such duration to an expected duration represented by the stored reference value information. For this type of comparison, it is helpful to design locking latch 34 and free-flow prevention device 16 such that plunger 38 moves at a substantially fixed velocity relative to carrier 40 so that the time duration is indicative of the plateau length L1 or L2 in the direction of movement of plunger 38. A first time interval T1 of the profile signal may be evaluated to determine whether or not the administration set is loaded and is authorized, and a second time interval T2 of the profile signal different from the first time interval T1 may be evaluated to determine the type of the administration set. As shown in FIG. 8, the first and second time intervals T1 and T2 may overlap one another, but this is an option, not a requirement.

Comparisons may involve some portions of the sensed profile signal, while disregarding at least one other portion of the profile signal. For example, a spike or dip in the amplitude of the profile signal at the transition portion 67 due to a bump or recess in cam surface 50 may be used as a primary comparison feature, a secondary comparison feature for confirmation, or not at all. Evaluation logic may also be "single step" in nature, whereby the entire sensed profile signal is compared to stored reference values to find a complete match; if no match is found, an error message is displayed and the pump is disabled. If a match is found, the administration set type is known and can be validated with respect to an entered infusion protocol. As will be understood, evaluation of a sensed profile signal, and logic implemented based on the evaluation, are subject to wide design variation.

The particular configuration of sensor 52 is also subject to design choice. While a strain gauge is illustrated in the drawings, sensor 52 may be a magnetic or capacitive displacement sensor, an optical displacement sensor, or an acoustic displacement sensor. Any type of sensor capable of measuring displacement of follower 54 may be used in practicing the present invention.

While the invention has been described in connection with exemplary embodiments, the detailed description is not intended to limit the scope of the invention to the particular forms set forth. The invention is intended to cover such alternatives, modifications and equivalents of the described embodiment as may be included within scope of the claims.

What is claimed is:

1. An administration set of a predetermined type for use with an infusion pump to administer a specified infusion protocol to a patient, wherein the predetermined type is chosen from a plurality of different administration set types, and wherein the infusion pump includes a follower, the administration set comprising:
   tubing for conveying an infusion liquid; and
   a free-flow prevention device operable to selectively stop and permit flow of the infusion liquid through the tubing;
   wherein the free-flow prevention device includes a carrier and a plunger movable relative to the carrier between an open position permitting flow of the infusion liquid through the tubing and a closed position stopping flow of the infusion liquid through the tubing, the plunger being biased toward the closed position and having a cam surface defining an uneven profile along a direction of movement of the plunger;

wherein the cam surface is exposed through a slot in the carrier and is slidably engageable by the follower, and the cam surface profile is configured to displace the follower in an elevation direction orthogonal to the direction of movement of the plunger as the plunger is moved from the closed position to the open position;

wherein the cam surface profile indicates the administration set is authorized for use with the infusion pump.

2. The administration set according to claim 1, wherein the cam surface profile further indicates the predetermined type of the administration set.

3. The administration set according to claim 2, wherein the cam surface profile includes a first plateau and a second plateau having different respective elevations.

4. The administration set according to claim 3, wherein the first plateau and the second plateau have different respective lengths in the direction of movement.

5. The administration set according to claim 3, wherein the cam surface profile further includes a topographical feature between the first plateau and the second plateau.

6. The administration set according to claim 5, wherein the topographical feature is a bump, a ramp, or a recess.

* * * * *